United States Patent [19]

Oda et al.

[11] Patent Number: 4,831,845
[45] Date of Patent: May 23, 1989

[54] TEMPERATURE TESTING DEVICE PROVIDED WITH SAMPLE-RECEIVING CHAMBER FROM WHICH A SPECIMEN IS EASILY DETACHABLE AND IN WHICH TEMPERATURE IS CONTROLLABLE

[75] Inventors: Yasukage Oda, Takatsuki; Hiroshi Asami, Hiratsuka, both of Japan

[73] Assignees: Yasukage Oda, Osaka; Sumitomo Heavy Industries, Ltd., Tokyo, both of Japan

[21] Appl. No.: 234,410

[22] Filed: Aug. 19, 1988

[30] Foreign Application Priority Data

Aug. 27, 1987 [JP] Japan ................................ 62-213329

[51] Int. Cl.[4] ............................................. F25B 19/00
[52] U.S. Cl. ..................................... 62/51.1; 374/176
[58] Field of Search ....................... 62/514 R; 374/176

[56] References Cited

U.S. PATENT DOCUMENTS

| | | | |
|---|---|---|---|
| 4,432,216 | 2/1984 | Matsuda et al. | 62/514 R |
| 4,498,046 | 2/1985 | Faris et al. | 62/514 R |
| 4,510,771 | 4/1985 | Matsuda et al. | 62/514 R |
| 4,578,963 | 4/1986 | Sitte | 62/514 R |
| 4,689,439 | 8/1987 | Sato | 62/514 R |
| 4,692,560 | 9/1987 | Hotta et al. | 62/514 R |

*Primary Examiner*—Ronald C. Capossela
*Attorney, Agent, or Firm*—Flynn, Thiel, Boutell & Tanis

[57] ABSTRACT

A temperature testing device in which a sample-receiving sealable chamber from which a specimen can be easily detached and a cooling portion of a refrigeration unit are inserted into a single vacuum vessel, and in which a gaseous refrigerant is circulated between the cooling portion of the refrigeration unit and the sample-receiving chamber so that the sample-receiving chamber can be cooled.

4 Claims, 1 Drawing Sheet

TEMPERATURE TESTING DEVICE PROVIDED WITH SAMPLE-RECEIVING CHAMBER FROM WHICH A SPECIMEN IS EASILY DETACHABLE AND IN WHICH TEMPERATURE IS CONTROLLABLE

BACKGROUND OF THE INVENTION

The present invention relates to a low-temperature testing device which is used for testing the temperature characteristics of specimens of, for example, superconducting materials, and particularly to a low-temperature testing device in which specimens can be easily changed and the temperatures of specimens can be arbitrarily controlled.

Recently, competition in development of superconducting materials has become progressively keener, and it is extremely important to test the characteristics such as the critical temperature of a newly developed material. Examples of devices that are generally used in the measurement of the critical temperature of a new material include a device in which a sample-receiving chamber provided adjacent to a cooling portion of a Grifford-McMahon refrigeration unit or an improved type thereof is received in an adiabatic vacuum vessel so that a specimen received in the chamber can be cooled by heat transfer through a gas or a solid and a device in which a vessel receiving liquid helium or liquid nitrogen and a sample-receiving chamber placed adjacent to the bottom of the vessel are provided in an adiabatic chamber typically having a vacuum layer so that a specimen placed in the sample-receiving chamber can be cooled by heat transfer to liquid helium or liquid nitrogen.

However, each time the specimen is changed, adiabatic vacuum in these conventional low-temperature testing devices must be broken, and the operation of the refrigeration machine in the former device must be stopped. Therefore, the conventional devices each have a disadvantage in that the low-temperature atmosphere in the sample-receiving chamber of each of the devices which is achieved by the preceding test cannot be retained for the next test, and the temperature of the sample-receiving chamber thus returns to room temperature each time the specimen is changed. Each of the conventional low-temperature testing devices also have a disadvantage in that the temperatures of the sample-receiving chamber and the specimen are not easily raised or lowered at a controlled rate and a wide range.

Therefore, it is an object of the present invention to provide a temperature testing device which is provided with a sample-receiving chamber in which a specimen can be changed without adiabatic vacuum being broken, and which can be always maintained at a low temperature.

It is another object of the present invention to provide a low-temperature testing device in which the temperature of a sample-receiving chamber and a specimen can be precisely and easily controlled over a wide range by cooling the sample-receiving chamber with a circulating gaseous refrigerant.

Other objects of the present invention will be made clear from the description below.

SUMMARY OF THE INVENTION

A low-temperature testing device to which the present invention relates comprises (a) a sample-receiving sealable chamber whose greater part is inserted into a vacuum vessel in which a cooling portion of a refrigeration unit is also inserted, (b) a pump for circulating a gaseous refrigerant which is provided outside the vacuum vessel, (c) a first pipe which causes the outlet side of a pump to connect to an inlet for the gaseous refrigerant provided in a lower portion of the sample-receiving chamber while passing through a heat exchanger provided on the cooling portion of the refrigeration unit and through a temperature control means and (d) a second pipe which causes an outlet for the gaseous refrigerant provided approximately at an intermediate position along the length of the sample-receiving chamber to connect to the inlet side of the pump. The first and second pipes are provided in the vacuum vessel in which the cooling portion of the refrigeration unit and the sample-receiving chamber are inserted.

In this low-temperature testing device, the gaseous refrigerant such as helium or nitrogen gas is sent through the first pipe by the pump provided outside the vacuum vessel, cooled in the cooling portion of the refrigeration unit while passing through the first pipe, supplied into the sample-receiving chamber from a lower portion thereof, and brought into contact with a specimen placed therein to cool it. The gaseous refrigerant is then discharged from the outlet provided at the intermediate portion of the sample-receiving chamber, is passed through the second pipe and is returned to the pump. Therefore, the gaseous refrigerant can be circulated through the first pipe, the sample-receiving chamber, and the second pipe.

BRIEF DESCRIPTION OF THE ATTACHED FIGURES

FIG. 1 is a sectional view of an embodiment of a temperature testing device to which the present invention relates.

DETAILED DESCRIPTION OF THE INVENTION

Figure 1:
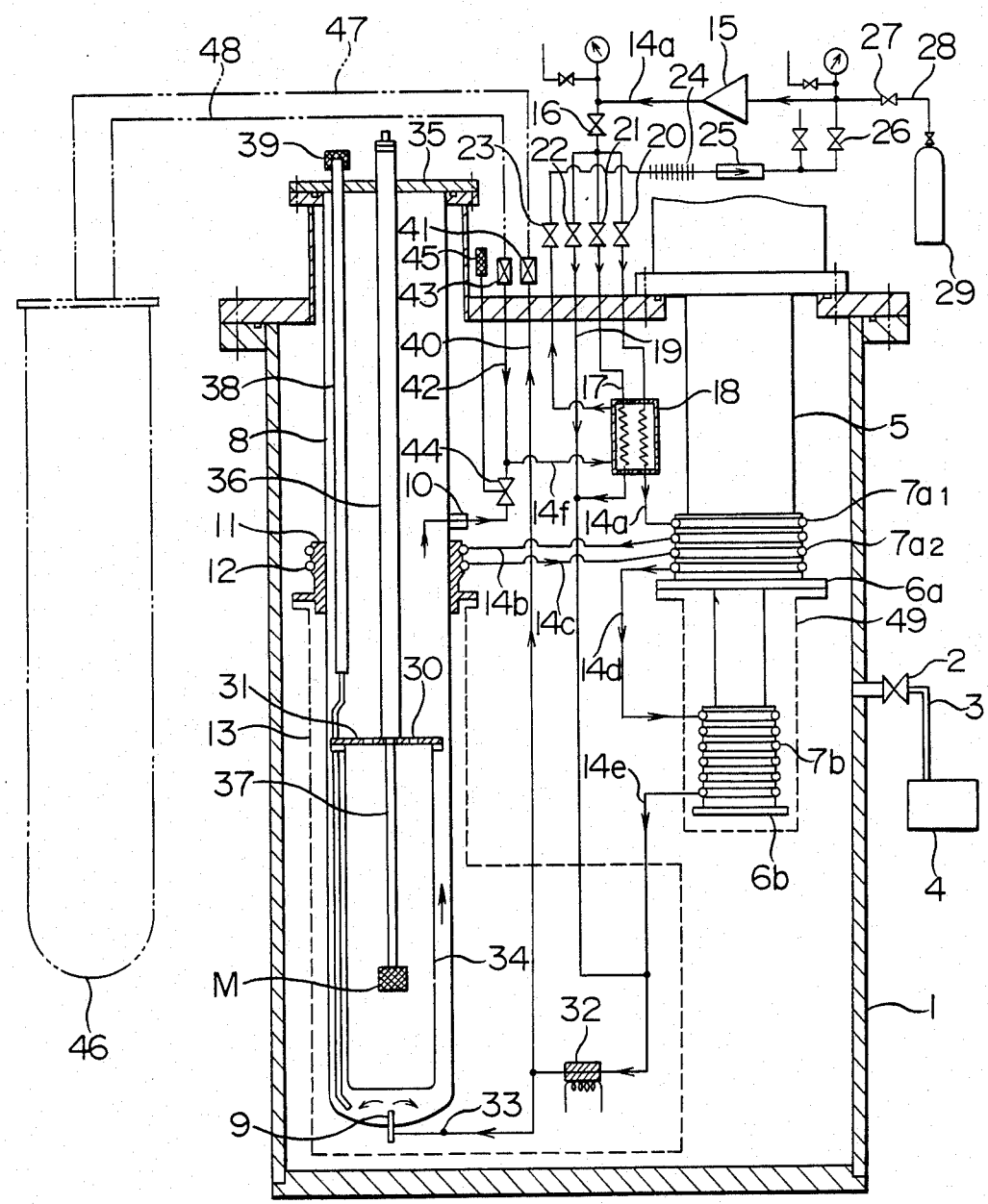

In the drawing, a vacuum pump 4 is connected to a vacuum vessel 1 by means of a pipe 3 through a valve 2. A two-stage refrigeration unit 5 employing the Gifford-McMahon cycle is inserted into the vacuum vessel 1, a first cooling stage 6a and a second cooling stage 6b thereof being placed in the vacuum vessel 1. The first cooling stage 6a has cooling coils $7a_1$ and $7a_2$ and the second cooling stage 6b has a cooling coil 7b, and the second cooling stage 6b and the cooling coil 7b are covered with a radiation shield 49. Similarly, a sample-receiving chamber 8 which has a cylindrical form with a bottom closed is inserted into the vacuum vessel 1. The sample-receiving chamber 8 has a gas inlet 9 and a gas outlet 10 which are provided on the bottom of the chamber 8 and at an intermediate position along the length thereof, respectively. A cooling stage 11 made of a band with excellent heat conductivity and a cooling coil 12 are provided approximately in an intermediate position between the top and the bottom of the sample-receiving chamber 8 lower than the position of the gas outlet 10. The portion of the sample-receiving chamber 8 below the cooling stage 11 is covered with a radiation shield 13.

Pipes 14a, 14b, 14c, 14d, 14e, 17 and 19 are pipes for supplying the gaseous refrigerant expelled from a circulating pump 15 which is provided on the outside of the vacuum vessel 1 to the gas inlet 9 at the bottom of the sample-receiving chamber 8. The pipe 14a connects the outlet side of the circulating pump 15 to the cooling coil $7a_1$ provided on the refrigeration unit 5 through valves 16, 20 and a precooler 18. The pipe 14b connects the cooling coil $7a_1$ to the cooling coil 12 provided on the sample-receiving chamber 8, and the pipe 14c connects the cooling coil 12 to the cooling coil $7a_2$. The pipe 14d connects the cooling coil $7a_2$ provided on the refrigeration unit 5 to the cooling coil 7b. The pipe 14e connects the cooling coil 7b to the gas inlet 9 of the sample-receiving chamber 8 through a temperature control means 32, typically a heater, and a thermometer 33. The pipe 19 causes the gaseous refrigerant supplied from the circulating pump 15 through the valves 16 and 22 to bypass without the refrigerant being passed through the precooler 18 and the cooling coils $7a_1$, 12, $17a_2$ and 7b so as to cause the gaseous refrigerant to combine with the pipe 14e. The pipe 17 causes the gaseous refrigerant supplied from the circulating pump 15 through the valves 16 and 21 to pass through the precooler 18 and then to combine with the pipe 19.

A pipe 14f connects the gas outlet 10 provided approximately at the intermediate position of the sample-receiving chamber 8 to the inlet side of the circulating pump 15 by way of the precooler 18, a valve 23, a radiator 24, a flow meter 25 and a flow control valve 26. A helium gas bomb 29 is connected to the inlet side of the circulating pump 15 by means of a pipe 28 having a valve 27.

Reference numeral 34 denotes a specimen-receiving vessel which can be freely inserted into and extracted from the sample-receiving chamber 8 and which is suspended by a hanger pipe 36 inserted through a cap 35 which is provided at the top of the sample-receiving chamber 8 and can be freely opened and closed. The specimen-receiving vessel 34 generally has a size which can be fit into the space between the bottom of the sample-receiving chamber 8 and the cooling stage 11. A specimen M positioned in the receiving vessel 34 is supported by a rod 37 which is connected to the hanger pipe 36, but the specimen M can be supported by any other support means in place of this rod 37. The specimen-receiving vessel 34 is generally covered with a cap 31 having an opening 30 at the top thereof.

A pipe 38 inserted into the sample-receiving chamber 8 is used when a liquid refrigerant such as liquid helium or liquid nitrogen is inserted into the receiving chamber 8, and a cap 39 is provided on the pipe 38.

A pipe 40 is used for discharging the gaseous refrigerant from the vacuum vessel 1, one end thereof being connected to a cap 41 and the other end being connected to the pipe 14e on the downstream side of the heater 32. A pipe 42 is used for returning the gaseous refrigerant used outside the vacuum vessel 1 in into the vacuum vessel 1, one end of the pipe 42 being connected to a cap 42 and the other end thereof being connected to the pipe 14f on the downstream side of a valve 44. The pipes 40 and 42 are connected to another sample-receiving chamber 46 through adiabatic pipes 47 and 48, respectively, so that the gaseous refrigerant which is at a temperature controlled by the device of the present invention can be supplied to another sample-receiving chamber provided outside the vaccuum vessel 1 by closing the valve 44 by means of a handle 45. In the embodiment shown in the drawing, the sample-receiving chamber and the cooling portion of the refrigeration unit are provided in the same vaccuum vessel, but they may be provided in individual vacuum vessels.

A description will now be made of a method of operating the low-temperature testing device.

The specimen M to be subjected to meaurement of its critical temperature and so on is received into the receiving vessel 34 which is suspended in the sample-receiving chamber 8 which is closed by the cap 35, as shown in the drawing. The air in the sample-receiving chamber 8 and in each of the pipes is then displaced by a helium gas. Then, after the valve 2 has been opened and the vacuum pump 4 has been operated so that the pressure in the vacuum vessel 1 is reduced to, for example, about $5 \times 10^{-2}$ torr, the refrigeration unit 5 is started. After the refrigeration unit 5 has reached a desired cooling level, in general, the valve 2 can be closed and the operation of the vacuum pump 4 can be stopped.

When the refrigeration unit 5 has cooled to the desired level, the valves 16, 20, 23, 44 and 26 are opened, the valves 21 and 22 are closed, and the circulating pump 15 is activated. The gaseous refrigerant which is discharged from the circulating pump 15 and is typically a helium gas is cooled to some extent by being passed through the precooler 18 and then further cooled by being passed through the cooling coil $7a_1$ of the first cooling stage of the refrigeration unit. The refrigerant passed through the coil $7a_1$ is passed through the pipe 14b and then through the cooling coil 12 provided on the sample-receiving chamber 8 from which it absorbs heat, and passed through the pipe 14c and through the cooling coil $7a_2$ where the refrigerant is again cooled. The refrigerant is then further cooled while being passed through the pipe 14d and through the cooling coil 7b provided on the second cooling stage of the refrigeration unit 5, passed through the pipe 14e and supplied to the receiving chamber 8 from the gas inlet 9 at the bottom thereof.

The gaseous refrigerant supplied to the receiving chamber 8 enters the vessel 34 from the openings in the cap 31 so as to cool the specimen M. The refrigerant is then sucked from the gas outlet 10, sent to the precooler 18 through the pipe 14f and returned to the inlet side of the circulating pump 15 through the valves 23 and 26. Therefore, the helium gas serving as the refrigerant is repeatedly circulated between a group of the cooling coils of the refrigeration unit and the sample-receiving chamber so that the specimen in the specimen-receiving vessel can be cooled by the cold refrigerant supplied from the bottom of the sample-receiving chamber 8 and by the cooling stage 11. In addition, the temperature in the receiving chamber 8 can be lowered from room temperature to about 10 K. due to the structure of the sample-receiving chamber in which the heat transfer between the sample-receiving chamber and the circumference thereof is inhibited by the radiation shield 13.

A method of measuring the critical temperature of a superconducting material is generally a method of measuring a critical temperature in which the temperature of a specimen is gradually raised from an extremely low temperature or a method of measuring a critical temperature in which the temperature of a specimen is gradually lowered from any desired temperature. The device of the present invention can be applied to either of these methods. When the former method is employed, the temperature in the sample-receiving chamber 8 is lowered to a given extremely low temperature in accordance with the aforementioned process, and the heater 32 is then operated while the temperature of the gaseous refrigerant supplied to the receiving chamber 8 being monitored by the thermometer 33. Although this is the simplest method, the temperature in the receiving chamber 8 can also be gradually raised by increasing the opening of the valve 21 or 22 while reducing the opening of the valve 20 so as to increase the ratio of the refrigerant bypassing the cooling coil group and flowing through the pipe 19 to the refrigerant passing through the cooling coil group of the refrigeration unit 5 and flowing through the pipe 14e. In this case, the temperature rise rate itself can be controlled by controlling the output of the heater 32 and/or the increase rate of the above-described ratio. When the latter method is employed, the temperature in the sample-receiving chamber 8 can be lowered at any desired rate in accordance with the process reverse to the aforementioned process.

One of the characteristics of the device of the present invention is the fact that the specimen can be easily exchanged while the operation of the device being continued, without the need for returning the temperature of the sample-receiving chamber 8 which is kept at the final stage in the preceding test to room temperature when the specimen is exchanged. In other words, the operations of the refrigeration unit 15 and the circulating pump 15 are continued, and the valve 27 is opened and the valve 23 or 44 is closed in the state wherein the helium gas refrigerant is circulated in the route flowing through the pipe 14d. The cap 35 of the receiving chamber 8 is then opened for the purpose of extracting the receiving vessel 34 therefrom. As a result, the system is replenished with the helium gas in the bomb 29 by the circulating pump 15, and the helium gas is cooled by being passed through the cooling coil group of the refrigeration unit 5, continuously supplied to the bottom of the receiving chamber 8, and expelled to the air from the top thereof. Therefore, the temperature of the receiving chamber is not returned to room temperature even if the cap 35 is removed from the sample-receiving chamber 8 when the specimen is exchanged, and thus no air and moisture enter the receiving chamber 8.

The above-described helium gas as well as a nitrogen gas can be used as the gaseous refrigerant used in the device of the present invention. However, use of the helium gas enables the specimen to be cooled to a lower temperature than use of the nitrogen gas. The flow rate and the pressure of the gaseous refrigerant which circulates in the device can be arbitrarily selected, but it is typically preferable to employ a flow rate of 10 to 50 l/min and a pressure of about 1 atm. Although the embodiment shown in the drawing uses the two-stage refrigeration unit using the Gifford-McMahon cycle, a Joule-Thomson circuit can be combined with the refrigeration unit in order to achieve an even lower temperature.

The gaseous refrigerant cooled in the device of the present invention can be employed outside the device. In this case, for example, the additional sample-receiving chamber 46 is caused to communicate with the pipes 40 and 42 by the adiabatic pipes 47 and 48, as shown in the drawing, by sealing the receiving chamber 8 and closing the valve 44. In addition, the device of the present invention is typically used for maintaining the specimen at a temperature within the range of room temperature to an extremely low temperature, but the device can be used for maintaining the specimen at a temperature higher than room temperature by using the heater 32 which is included in the device. The device can also be used for maintaining the specimen at a constant temperature of about 4 k. or about 77 K. by stopping the circulation of the gaseous refrigerant and introducing liquid helium or liquid nitrogen from the pipe of the sample-receiving chamber 8.

What is claimed is:

1. A temperature testing device comprising:
   (a) a vacuum vessel;
   (b) an elongated vertical chamber adapted to receive a sample, substantially most part of which is inserted into said vacuum vessel and having an opening with a cap exposed outside said vacuum vessel;
   (c) a refrigeration unit with a cooling portion which is provided in said vacuum vessel;
   (d) a pump which is provided outside said vacuum vessel and is used for circulating a gaseous refrigerant;
   (e) a first pipe which connects the outlet side of said pump to a gas inlet provided in the vicinity of the bottom of said sample-receiving chamber while passing through a heat exchanger provided on said cooling portion of said refrigeration unit and passing through a temperature control means so that said gaseous refrigerant expelled from said pump is supplied to said sample-receiving chamber; and
   (f) a second pipe which connects a gas outlet provided substantially in an intermediate portion of said sample-receiving chamber in the lengthwise direction thereof to a inlet side of said pump so that said gaseous refrigerant in said sample-receiving chamber is returned to said pump.

2. A device according to claim 1, wherein said sample-receiving chamber has a heat exchanger provided in the vicinity of said gas outlet thereof and a pipe which causes said heat exchanger thereof to communicate with said heat exchanger of said cooling portion of said refrigeration unit.

3. A device according to claim 1, wherein said sample-receiving chamber is provided with a pipe for a liquid refrigerant.

4. A device according to claim 1, wherein an indirect heat exchanger between the refrigerant flowing through said first pipe and the refrigerant flowing said second pipe is provided on the upperstream side of said heat exchanger of said first pipe.

* * * * *